(12) United States Patent
Bhunia et al.

(10) Patent No.: US 8,818,505 B2
(45) Date of Patent: Aug. 26, 2014

(54) PHYSIOLOGICAL PERTURBATIONS FOR MEASURING HEART FAILURE

(75) Inventors: Sourav K. Bhunia, Shoreview, MN (US); Paul D. Ziegler, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 13/614,004

(22) Filed: Sep. 13, 2012

(65) Prior Publication Data

US 2013/0079646 A1 Mar. 28, 2013

Related U.S. Application Data

(60) Provisional application No. 61/540,276, filed on Sep. 28, 2011.

(51) Int. Cl.
*A61N 1/36* (2006.01)
(52) U.S. Cl.
USPC .................................................. 607/9
(58) Field of Classification Search
None
See application file for complete search history.

(56) References Cited

U.S. PATENT DOCUMENTS

| 4,374,382 | A | 2/1983 | Markowitz |
| 5,117,824 | A | 6/1992 | Keimel et al. |
| 5,545,186 | A | 8/1996 | Olson et al. |
| 5,755,736 | A | 5/1998 | Gillberg et al. |
| 6,102,874 | A | 8/2000 | Stone et al. |
| 6,104,949 | A | 8/2000 | Pitts Crick et al. |
| 6,572,557 | B2 | 6/2003 | Tchou et al. |
| 7,177,684 | B1 | 2/2007 | Kroll et al. |
| 2002/0115939 | A1* | 8/2002 | Mulligan et al. ............... 600/510 |
| 2003/0212445 | A1* | 11/2003 | Weinberg ........................ 607/116 |
| 2007/0021678 | A1 | 1/2007 | Beck et al. |
| 2011/0106201 | A1 | 5/2011 | Bhunia |
| 2011/0172545 | A1* | 7/2011 | Grudic et al. .................. 600/485 |
| 2012/0109237 | A1 | 5/2012 | Xiao et al. |

* cited by examiner

*Primary Examiner* — Carl H Layno
*Assistant Examiner* — Ankit Tejani
(74) *Attorney, Agent, or Firm* — Michael C. Soldner

(57) ABSTRACT

Techniques of inducing a physiological perturbation to monitor a heart failure status of a patient are described. An implantable medical device (IMD) may induce a physiological perturbation in the patient to monitor and determine how the patient responds to the physiological change. This response may be indicative of heart failure improvement or worsening. For example, the IMD may deliver electrical stimulation with parameters configured to perturb the patient (e.g., stimulation that deviates from stimulation therapy). The IMD may then detect at least one physiological parameter to monitor the patient's response to the perturbation. Based on the detected physiological parameter, the IMD may generate a heart failure status. The heart failure status may then be used for adjusting patient therapy, with or without the use of remote monitoring.

16 Claims, 10 Drawing Sheets

PHYSIOLOGICAL PERTURBATIONS FOR MEASURING HEART FAILURE

CROSS-REFERENCE TO PRIORITY APPLICATION

The present application claims priority and other benefits from U.S. Provisional Patent Application Ser. No. 61/540,276, filed Sep. 28, 2011, incorporated herein by reference in its entirety.

TECHNICAL FIELD

The invention relates to medical devices, and, more particularly, to medical devices that monitor cardiac health.

BACKGROUND

Heart failure is a condition affecting thousands of people worldwide. Essentially, congestive heart failure occurs when the heart is unable to pump blood at an adequate rate in response to filling pressure. This condition may result in congestion in the tissue, peripheral edema, pulmonary edema, and even shortness of breath. When heart failure is severe, it can even lead to patient death.

Although heart failure treatments may include electrical stimulation therapy and drug therapy, drug therapy has been the more effective treatment for most patients. For example, patients suffering from or at risk for heart failure may be treated with diuretic agents and/or angiotensin converting enzyme inhibitors. In addition, patients may be treated with nitroglycerin to reduce the symptoms of heart failure. Even though treatments are available, patients with other cardiac conditions may be at greater risk of severe complications with the conditions of heart failure.

SUMMARY

Generally, this disclosure describes techniques for inducing a physiological perturbation to monitor a heart failure status of a patient. The physiological perturbation that is induced within the patient may be any alteration or challenge to the patient physiology. In response to this perturbation, one or more parameters of the patient may change (e.g., the patient's body may attempt to correct or otherwise accommodate for the perturbation). Depending on the heart failure status of the patient, the patient may respond differently to the perturbation. In other words, the monitored response of the one or more parameters to the physiological perturbation may indicate that the patient's heart failure is improving, not changing, or worsening. Treatment of the patient may thus be changed based on the detection of one or more parameters in response to the perturbation.

For example, an implantable medical device (IMD) may induce a physiological perturbation in the patient and monitor the patient's response to the physiological perturbation. The perturbation induced by the IMD may be caused by the delivery of electrical stimulation with parameters configured to perturb the patient. In examples in which the IMD delivers therapeutic electrical stimulation, the parameters of the perturbation stimulation may deviate from parameters for the therapeutic stimulation by a predetermined magnitude. The IMD may then detect at least one physiological parameter to monitor the patient's response to the perturbation. Based on the detected physiological parameter, the IMD may generate a heart failure status. The heart failure status may then be monitored remotely and the patient's therapy may be adjusted (e.g., stimulation therapy, pharmacological therapy, diet, and/or instructed activity).

In one example, the disclosure describes a method that includes inducing a physiological perturbation in a patient, detecting a change in at least one physiological parameter of the patient in response to the induced physiological perturbation, and generating a heart failure status based on the detected change in the at least one physiological parameter.

In another example, the disclosure describes a system that includes a perturbation module configured to induce a physiological perturbation in a patient, and a sensing module configured to detect a change in at least one physiological parameter of the patient in response to the induced physiological perturbation, wherein the perturbation module is configured to generate a heart failure status based on the change to the at least one physiological parameter.

In another example, the disclosure describes a system that includes means for inducing a physiological perturbation in a patient, means for detecting a change in at least one physiological parameter of the patient in response to the induced physiological perturbation, and means for generating a heart failure status based on the change to the at least one physiological parameter.

The details of one or more examples are set forth in the accompanying drawings and the description below. Other features, objects, and advantages will be apparent from the description and drawings, and from the claims.

DETAILED DESCRIPTION

Figure 1:
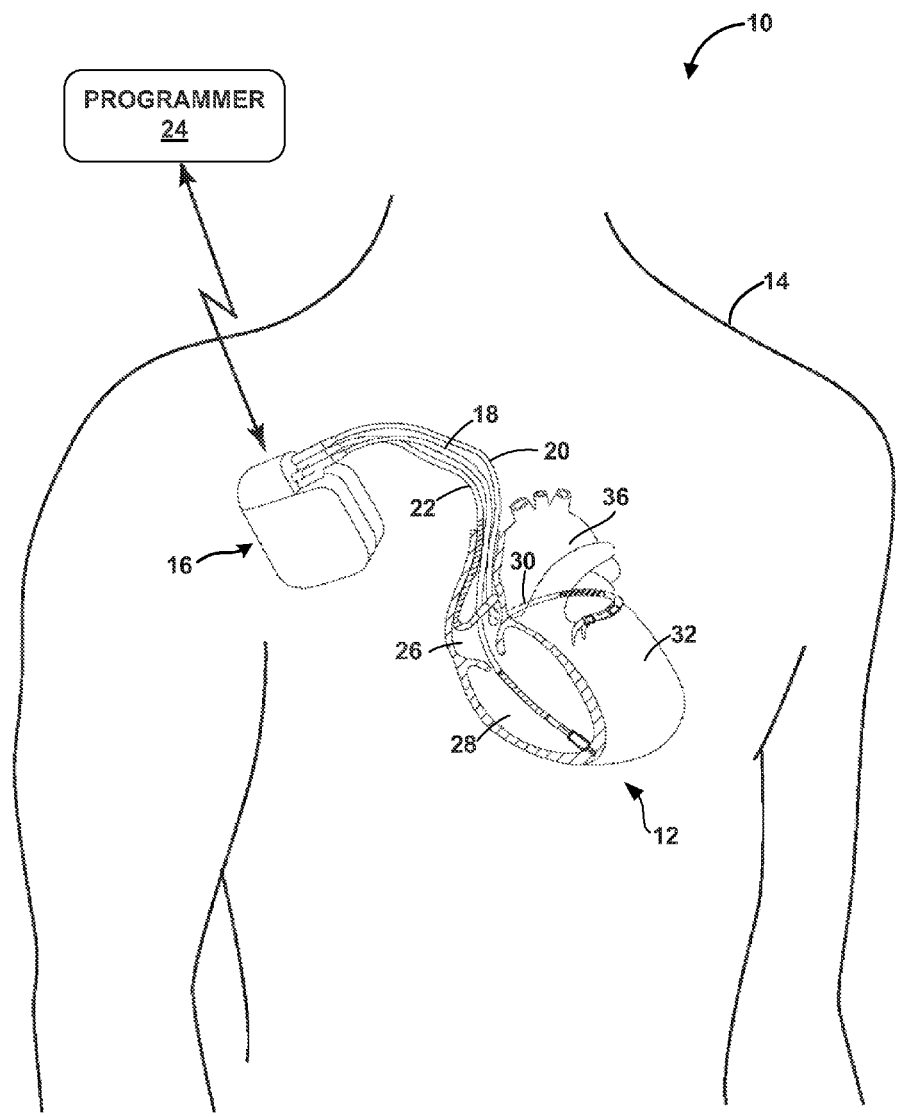
FIG. 1 is a conceptual drawing illustrating an example system configured to induce a physiological perturbation and generate a heart failure status with an implantable medical device (IMD) coupled to implantable medical leads.

Generally, this disclosure describes techniques for inducing a physiological perturbation to monitor a heart failure status of a patient. Congestive heart failure may occur, and worsen, over time due to heart disease, patient inactivity, cardiac arrhythmias, hypertension, and other conditions. Often, however, a relatively rapid worsening of the patient's condition, e.g., a decompensation, may occur in patients already being treated for heart failure.

A heart failure status of the patient (e.g., the level or severity of heart failure) may be monitored during patient exercise or exertion. Heart rate variability, for example, may be detected when the patient is at rest and when the patient is exercising as one indicator of any change in heart failure. A decrease in heart rate variability during exercise may indicate worsening heart failure. However, the exertion level at which the patient exercises each time varies, and is not easily extracted from collected data, e.g., from accelerometer data. Even if the patient indicates the perceived exertion level for the exercise, this exertion level is subjective and may not be an accurate indication of the physiological challenge.

As described herein, an induced physiological perturbation may be controlled to generate a more accurate determination of the heart failure status of the patient. The physiological perturbation that is induced within the patient may be any alteration or challenge to the patient physiology. In other words, physiological systems may, in healthy patients, respond to this induced perturbation. In response to this perturbation, the one or more parameters of the patient may change (e.g., the patient's body may attempt to correct or otherwise accommodate for the perturbation). Depending on the heart failure status of the patient, the patient may respond differently to the perturbation. Monitoring one or more parameters for any change in response to the physiological perturbation may indicate that the patient's heart failure is improving, not changing, or worsening. Based on the detected changes in patient parameters, the system may generate a heart failure status. Treatment of the patient may thus be changed based on the detection of one or more parameters in response to the perturbation.

In one example, an implantable medical device (IMD) e.g., a pacemaker, cardioverter and/or defibrillator, may induce a physiological perturbation in the patient, monitor the patient's response to the physiological perturbation, and transmit the monitored patient response and/or a heart failure status generated based thereon to a remote device for review by a clinician. The IMD may deliver electrical stimulation defined by stimulation parameters selected to induce the physiological perturbation in the patient. The stimulation parameters for the perturbation may deviate from stimulation therapy parameters that define stimulation therapy by a predetermined magnitude. In other words, the perturbation stimulation may be sufficiently different from stimulation therapy generally delivered by the IMD to treat the patient. Example electrical stimulation to induce physiological perturbations may include changes to the atrial pacing rate, ventricular pacing rate, modifications to the atrial-ventricular intervals, modifications to the ventricular-ventricular intervals, suspension of cardiac resynchronization therapy pacing, slowing the heart rate by cardiac electrical window therapy, or any combination thereof. These changes are merely example changes, as the perturbation stimulation may be defined as any stimulation defined by at least one or more parameters different than that of a stimulation therapy. For example, the atrial rate or the ventricular rate may be increased or decreased by a certain amount, such as 20%, the AV interval may be increased by 100% or decreased by 50%, the VV interval may be increased or decreased by 100 ms, and the cardiac output may be decreased by 20%. A drug pump may also be utilized to affect rates, intervals and cardiac output, using thresholds described above, by adjusting the dosage of the drug. However, the amount by which the drug dosage is changed would be highly dependent upon the particular drug involved.

Once the perturbation stimulation is delivered, the IMD may detect at least one physiological parameter indicative of heart failure (e.g., heart rate, blood pressure, intrathoracic impedance, or heart rate variability) to monitor the patient's response to the perturbation. Example physiological parameters indicative of heart failure are described in U.S. Patent Publication No. 2011/0106201 to Sourav Bhunia, entitled "IMPLANTABLE HEART FAILURE MONITOR," the entire content of which is incorporated herein by reference. Based on the detected physiological parameter, the IMD, an external programmer, a monitor, or even a remote server (e.g., a computing device remote from the patient) may generate a heart failure status. The heart failure status may then be transmitted and used for remote monitoring of the patient.

The heart failure status may elicit a change in therapy for the patient. For example, the IMD may be reprogrammed such that one or more therapy parameters are adjusted to better treat the heart failure of the patient. Alternatively, the patient's pharmacological therapy, diet, and/or instructed activity may be modified by the clinician. Since heart failure can worsen in a relatively short period of time, remote monitoring of the patient's heart failure status may improve therapy efficacy, quality of life, and life expectancy.

In some examples, the IMD may adjust the stimulation parameters that define the perturbation stimulation delivered by the IMD. If the IMD determines that detected physiological parameters are not indicating that a sufficient perturbation has been induced, the IMD may automatically increase the perturbation setting, e.g., the deviation of one or more stimulation parameters from regularly-delivered therapy parameters. This adjustment of the perturbation may improve the ability of the IMD to accurately determine the heart failure status. In other examples, the stimulation therapy delivered to the patient by IMD may be adjusted based on the detected physiological parameters after the perturbation. For example, the IMD may adjust the V-V interval (i.e., the right ventricle to left ventricle interval) due to sensed patient activity if heart failure is worsening.

The IMD may deliver perturbation stimulation immediately following stimulation therapy to induce the physiological perturbation. However, stimulation therapy may change over time as the patient requires different therapy to adequately treat one or more conditions. Therefore, the difference between the perturbation stimulation and therapy stimulation may change over time, which may complicate comparisons between physiological parameter changes from one induced perturbation to a different induced perturbation. To address such complications, the IMD may thus deliver consistent baseline stimulation, which may have stimulation parameters different then the present therapeutic stimulation parameters, to the patient prior to inducing the physiological perturbation. Although the therapeutic stimulation parameters may change, the parameters of the baseline stimulation may not change over the entire therapy or monitoring period of the patient. Once the baseline stimulation is delivered, the IMD may then deliver electrical stimulation to induce the physiological perturbation. Although the baseline stimulation therapy may be delivered for a predetermined period of time, the IMD may deliver the baseline stimulation until detected physiological parameters become stable or otherwise accustomed to the baseline stimulation.

In general, this disclosure describes physiological perturbations being induced by electrical stimulation from an IMD. However, the systems disclosed herein may incorporate alternative, or additional, techniques for inducing the physiological perturbations. As examples, a drug delivery device may deliver a drug to the patient, a ventricular-assist device may mechanically alter the blood flow output from the heart, or another device may mechanically inhibit or enhance movement of one or more anatomical structures. In other examples, a device may instruct the patient to ingest a drug or perform a specified activity. Although the physiological perturbation may be induced by stimulating the patient, the physiological perturbation may instead be induced by removing or stopping a stimulus (e.g., stopping cardiac pacing therapy). In any of these examples, the stimulus provided or removed from the patient may be repeated to provide accurate tracking of heart failure progression over time.

FIG. 1 is a conceptual drawing illustrating example system 10 configured to induce a physiological perturbation and generate a heart failure status with implantable medical device (IMD) 16. In the example of FIG. 1, system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

Although an implantable medical device and delivery of electrical stimulation to heart 12 are described herein as examples, the techniques for inducing a physiological perturbation in patient 14 of this disclosure may be applicable to other medical devices and/or other techniques. In general, the techniques described in this disclosure may be implemented by any medical device, e.g., implantable or external, that is configured to induce some change in the patient that will elicit a measurable or detectable physiological change. As one alternative example, the techniques described herein may be implemented in an implantable drug pump that delivers a drug to patient 14 that induces a physiological perturbation.

In the example of FIG. 1, leads 18, 20, and 22 extend into the heart 12 of patient 14 to sense electrical activity of heart 12 and/or deliver electrical stimulation to heart 12 (e.g., stimulation therapy and/or perturbation stimulation). Leads 18, 20, and 22 may also be used to detect a thoracic impedance indicative of fluid volume in patient 14, respiration rates, sleep apnea, or other patient parameters. Respiration rates and sleep apnea may also be detectable via an electrogram. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient parameter for identifying a heart failure status.

IMD 16 may sense electrical signals attendant to the depolarization and repolarization of heart 12 via electrodes (not shown in FIG. 1) coupled to at least one of the leads 18, 20, and 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, and 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient parameters used in generating the heart failure status. IMD 16 may utilize two of any electrodes carried on leads 18, 20, and 22 to generate electrograms of cardiac activity. In some examples, IMD 16 may also use one or more housing electrodes of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor physiological parameters such as heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance. An example system for measuring thoracic impedance is described in U.S. Pat. No. 6,104,949 to Pitts Crick et al., entitled, "MEDICAL DEVICE," which issued on Aug. 15, 2000 and is incorporated herein by reference in its entirety. IMD 16 may use this impedance to create a fluid index indicative of heart failure status. By monitoring the fluid index in addition to other physiological parameters, IMD 16 may be able to identify the progression of heart failure in patient 14.

IMD 16 may also communicate with external programmer 24. In some examples, programmer 24 comprises a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding physiological parameter data and/or the heart failure status. Although programmer 24 may retrieve this information, IMD 16 may push or transmit the heart failure status if the heart failure status indicates a substantial change over a previous heart failure status or the heart failure status exceeds a threshold. Although IMD 16 may generate the heart failure status, IMD 16 may transmit the detected physiological parameter data to programmer 24 so programmer 24 may generate the heart failure status in other examples. Programmer 24 may present an alert to the user with the heart failure status and/or other physiological parameter data. This physiological parameter data may include intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts to facilitate immediate notification of the heart failure status.

Programmer 24 may allow the user to define how IMD 16 induces the physiological perturbation in patient 14. In one example, the user may define specific simulation parameters for the perturbation stimulation. In another example, the user may define a deviation from one or more therapy parameters to define the perturbation stimulation. In addition, the user may use programmer 24 to determine when the perturbation stimulation should be delivered to patient 14. In any case, the user may be able to initially set-up and/or modify the electrical stimulation used to induce the physiological perturbation in patient 14.

Programmer 24 may also allow the user to define how IMD 16 senses, detects, and manages each of the physiological parameters. For example, the user may define the frequency of sampling or the evaluation window used to monitor the physiological parameters.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

As described herein, IMD 16 (or another component of system 10) may induce a physiological perturbation in patient 14. This physiological perturbation may be any challenge or disruption to one or more body systems. Although patient 14 may be able to feel the physiological perturbation, IMD 16 may be able to induce the physiological perturbation without patient 14 being able to feel the induced perturbation. IMD 16 may include one or more sensors that detect at least one physiological parameter of patient 14 subsequent to inducing the physiological perturbation. IMD 16, external programmer 24, or another external device, may then generate a heart failure status for patient 14 based on at least one of the detected physiological parameters.

Generally, the physiological perturbation may be induced via IMD 16 delivering electrical stimulation to patient 14 for a predetermined period of time. The predetermined period of time may be selected based on clinician experience or modeling of the time needed for the physiological perturbation to be induced by the electrical stimulation. Alternatively, IMD 16 may deliver the electrical stimulation until detected physiological parameters indicate that the physiological perturbation has been induced. In this example, IMD 16 may detect one or more physiological parameters prior to delivery of the electrical stimulation and stop the electrical stimulation once at least one physiological parameter has exceeded a perturbation threshold. This feedback may ensure that IMD 16 induces the physiological perturbation in patient 14.

In some examples, IMD 16 may time the delivery of electrical stimulation, and induced physiological perturbation, to correspond to a particular activity state of patient 14. Perturbations to patient 14 may have varying effects on physiological parameters depending upon the activity state of patient 14. In a rest rate, physiological parameters may change less in response to the induced physiological perturbation. However, physiological changes due to patient exertion may be an added input to the perturbation that affects and complicates detection of the change in the physiological parameters due to the physiological perturbation. Conversely, IMD 16 may detect an active state of patient 14 and induce the physiological perturbation during this active state. Since the higher exertion level of patient 14 in the active state over the rest state may magnify the effects of the physiological perturbation, IMD 16 may more easily detect changes to the physiological parameters when the perturbation is delivered during the active state. A rest state of patient 14 may be when patient 14 is sitting or lying down, while the active state may be defined when patient 14 is walking, running, or otherwise engaged in physical activity.

The clinician may determine if IMD 16 delivers the perturbation stimulation during the active state or during the rest state. In some examples, IMD 16 may deliver the perturbation stimulation during the active state when heart failure is less severe to ensure detection of changed physiological parameters. However, IMD 16 may deliver the perturbation stimulation during the rest state when heart failure has worsened to get a more accurate determination of the heart failure status. Alternatively, IMD 16 may deliver electrical stimulation to induce the physiological perturbation during both the rest state and the active state to determine in which state patient 14 is more susceptible or responsive to the physiological perturbation.

The electrical stimulation may be a perturbation electrical stimulation that is defined by a plurality of stimulation parameters. These stimulation parameters may be the same parameters of stimulation therapy, e.g., an atrial rate, a ventricular rate, an A-V interval, a V-V interval, a pulse rate, a pulse amplitude, a pulse width, and an electrode combination. At least one of the stimulation parameters for the perturbation stimulation may have a perturbation value. This perturbation value may deviate from a therapeutic value of the same parameter used to at least partially define electrical stimulation therapy. For example, the therapeutic value for an escape interval may be approximately 1000 milliseconds, but the perturbation value for escape interval may be lower, e.g., approximately 800 milliseconds. Therefore, the perturbation value may deviate from the therapeutic value. In some examples, two or more stimulation parameters may deviate between the perturbation parameters and the therapy parameters.

The perturbation value may deviate from the therapeutic value by a magnitude between approximately 5 percent and 50 percent. In one example, the perturbation value deviates from the therapeutic value by at least 20 percent. However, the perturbation value may deviate from the therapeutic value by less than 5 percent or greater than 50 percent in other examples. The deviation of the perturbation value may be determined to be as small a deviation as necessary to induce the physiological perturbation. In alternative examples, the physiological perturbation may be induced by completely terminating all electrical stimulation from regularly delivered stimulation therapy.

Based on the one or more detected physiological parameters, IMD 16 or programmer 24 may adjust a value of at least one stimulation parameter that defines the electrical stimulation for the physiological perturbation. A memory within IMD 16 and/or programmer 24 may store the adjusted value for subsequent perturbation stimulation delivery. If the delivered electrical stimulation fails to induce a physiological perturbation, for example, IMD 16 may increase the deviation of one or more stimulation parameters from the therapeutic values and re-deliver the electrical stimulation. In some examples, the re-delivery of electrical stimulation may occur immediately after adjusting the value of the stimulation parameter for perturbation. In other examples, IMD 16 may wait until the next scheduled or determined time for inducing a physiological perturbation to deliver electrical stimulation for perturbation with the adjusted stimulation parameter value. This elapsed time, or lockout period, may allow the physiological systems of patient 14 to recover from the attempted perturbation.

As described herein, IMD 16 may also deliver electrical stimulation therapy to patient 14. Electrical stimulation therapy may differ from electrical stimulation that induces a physiological perturbation in one or more aspects. The therapy parameters that define the electrical stimulation therapy may be selected to treat patient 14 of a condition, e.g., bradycardia or heart failure, but the stimulation parameters of the perturbation stimulation may be selected to disrupt or perturb patient 14 to elicit a detectable change in one or more physiological parameters. The perturbation stimulation may also be delivered for a relatively short duration (e.g., less than 5 minutes) while the stimulation therapy may be delivered over periods of days, weeks, or even months. In some examples, consistent therapeutic stimulation is periodically interrupted by relatively short periods of perturbation stimulation delivery. In addition, the values of one or more of the parameters that define each of the stimulation therapy and perturbation stimulation may deviate from one another. The specific electrodes used to deliver the stimulation therapy may also, but not necessarily, be different from the specific electrodes used to deliver the perturbation stimulation.

In some examples, IMD 16 and/or programmer 24 may adjust at least one of a plurality of therapy parameters that define stimulation therapy based on at least one of the detected physiological parameter and the heart failure status. If IMD 16 is configured to provide therapy to patient 14, the detected physiological parameters and/or heart failure status may be used as feedback to adjust therapy parameters. For example, IMD 16 may adjust cardiac resynchronization therapy (CRT) timing based on the improvement or worsening of intrathoracic fluid levels and/or heart failure status.

The induced physiological perturbation may also be affected by any stimulation delivered to patient 14 prior to the perturbation stimulation. As described herein, IMD 16 may deliver electrical stimulation therapy to patient 14 prior to inducing the physiological perturbation. Therefore, IMD 16 may deliver baseline electrical stimulation to patient 14 after delivering stimulation therapy and prior to delivering the electrical stimulation that induces the physiological perturbation. This baseline electrical stimulation may condition patient 14 into a steady state that is generally consistent over time. Therefore, any changes to stimulation therapy over time may not affect the comparison between detected physiological parameters from different physiological perturbations. The electrical stimulation therapy may be defined by therapy parameters adjustable over time to treat the patient. In contrast, the baseline electrical stimulation may be defined by preselected therapy parameters that establish repeatable baseline electrical stimulation for each inducement of the physiological perturbation.

Although FIG. 1 is directed to IMD 16 inducing the physiological perturbation, other devices may induce the physiological perturbation in other examples. For example, a second implantable device in communication with IMD 16 may deliver an electrical or pharmaceutical stimulus configured to induce a physiological perturbation in patient 14. In other examples, programmer 24 may alternatively, or additionally, instruct patient 14 to perform some action to induce the physiological perturbation. For example, programmer 24 may instruct patient 14 to run before IMD 16 delivers the perturbation stimulation.

In various examples described herein, certain functionalities may be described with respect to one component or device of system 10. However, many functionalities described herein may be provided by other devices or components. For example, IMD 16 may be described as generating a heart failure status from the detected physiological parameters. However, other devices, such as programmer 24 or a remote computing device, may generate the heart failure status from transmitted physiological parameter data.

Although IMD 16 is described as an electrical stimulator for cardiac stimulation therapy, IMD 16 may alternatively be an electrical stimulator configured to deliver electrical stimulation to other tissues of patient 14. For example, IMD 16 may be a neurostimulator configured to deliver electrical stimulation to a nerve or muscle. In other examples, IMD 16 may be a drug pump that delivers pharmacological stimulation to patient 14. These, and combinations thereof, may be used induce a physiological perturbation in patient 14.

Figure 2A:
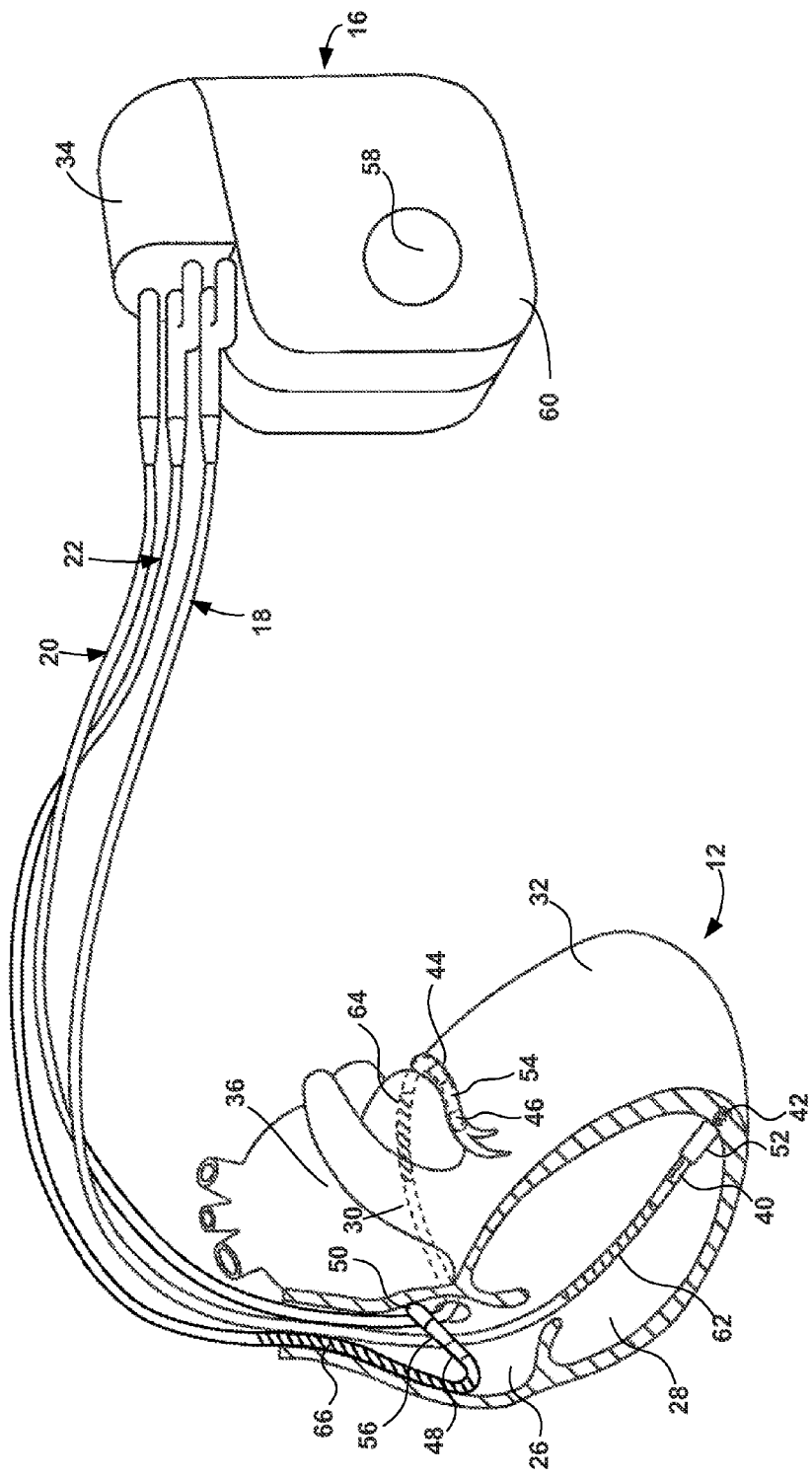
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, and 22 may be electrically coupled to a signal generator, e.g., stimulation generator, and a sensing module of IMD 16 via connector block 34. In some examples, proximal ends of leads 18, 20, and 22 may include electrical contacts that electrically couple to respective electrical contacts within connector block 34 of IMD 16. In addition, in some examples, leads 18, 20, and 22 may be mechanically coupled to connector block 34 with the aid of set screws, connection pins, snap connectors, or another suitable mechanical coupling mechanism.

Each of the leads 18, 20, and 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, and 22 also include elongated electrodes 62, 64, and 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, and 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, and 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, and 66 may also be used to deliver cardioversion pulses to heart 12. Electrodes 62, 64, and 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, and 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12. Further, external electrodes or other sensors may be used by IMD 16 to deliver therapy to patient 14 and/or sense and detect physiological parameters used to generate a heart failure status.

Figure 2B:
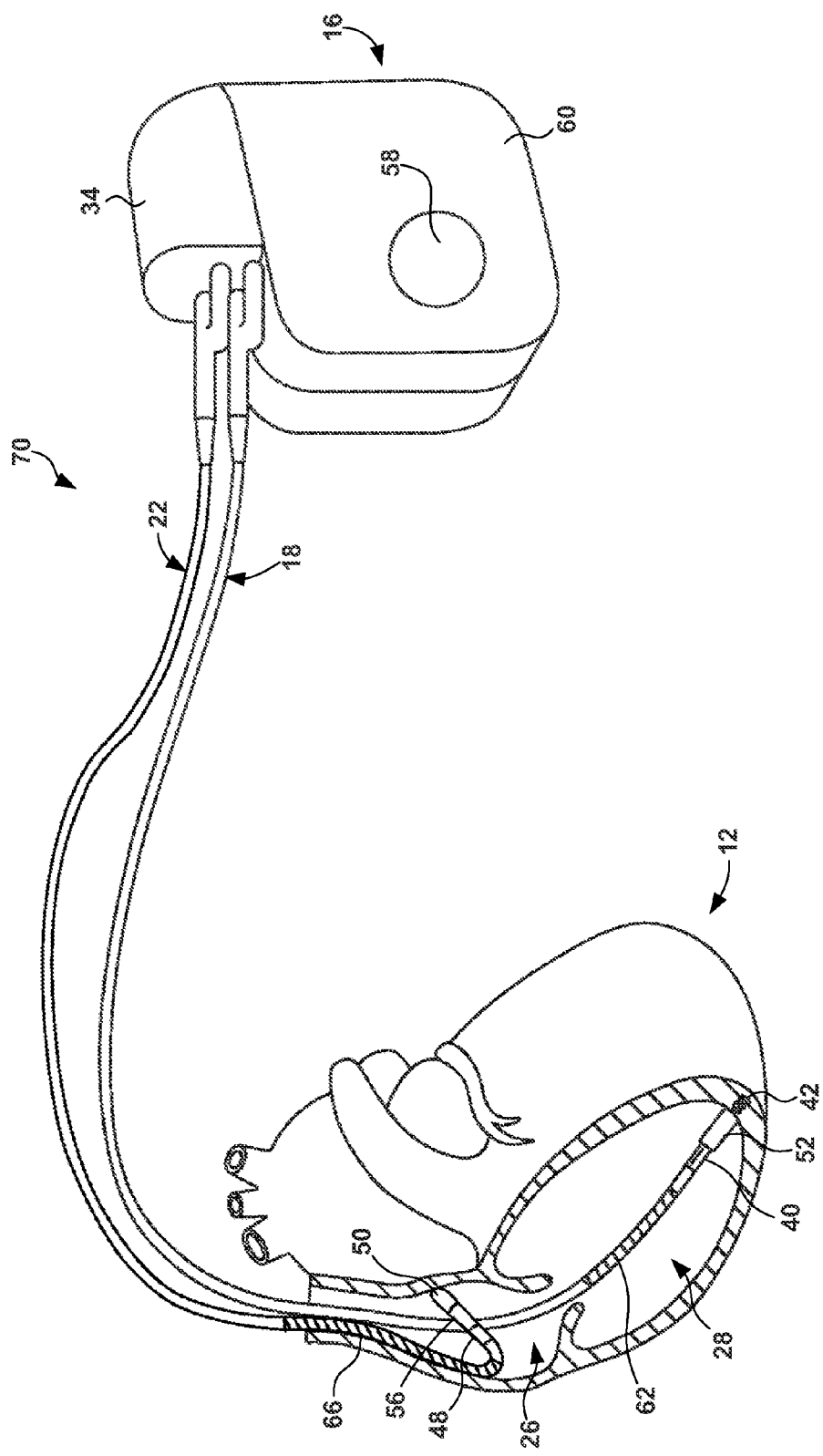
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to sense or detect physiological parameters used to generate the heart failure status for patient 14. Typically, IMD 16 may detect and collect physiological parameters from those electrode vectors used to treat patient 14. For example, IMD 16 may derive an atrial fibrillation duration, heart rate, and heart rate variability parameters from electrograms generated to deliver pacing therapy and or induce physiological perturbations. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. This intrathoracic impedance may be used to generate a fluid index physiological parameter that indicates the amount of fluid building up within patient 14. Since a greater amount of fluid may indicate increased pumping loads on heart 12, the fluid index may be used as an indicator of heart failure status. IMD 16 may periodically measure the intrathoracic impedance to identify a trend in the fluid index over days, weeks, months, and even years of patient monitoring.

In general, the two electrodes used to measure the intrathoracic impedance may be located at two different positions within the chest of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2, but includes two leads 18 and 22, rather than three leads. Leads 18 and 22 are implanted within right ventricle 28 and right atrium 26, respectively. System 70 shown in FIG. 2B may be useful for physiological sensing and/or providing pacing, cardioversion, or other therapies to heart 12. Inducing physiological perturbations and/or detecting physiological parameters according to this disclosure may be performed in two lead systems in the manner described herein with respect to three lead systems. In other examples, a system similar to systems 10 and 70 may only include one lead (e.g., any of leads 18, 20 or 22) to deliver therapy and/or sensor and detect patient metrics related to monitoring status of heart failure.

Figure 3:
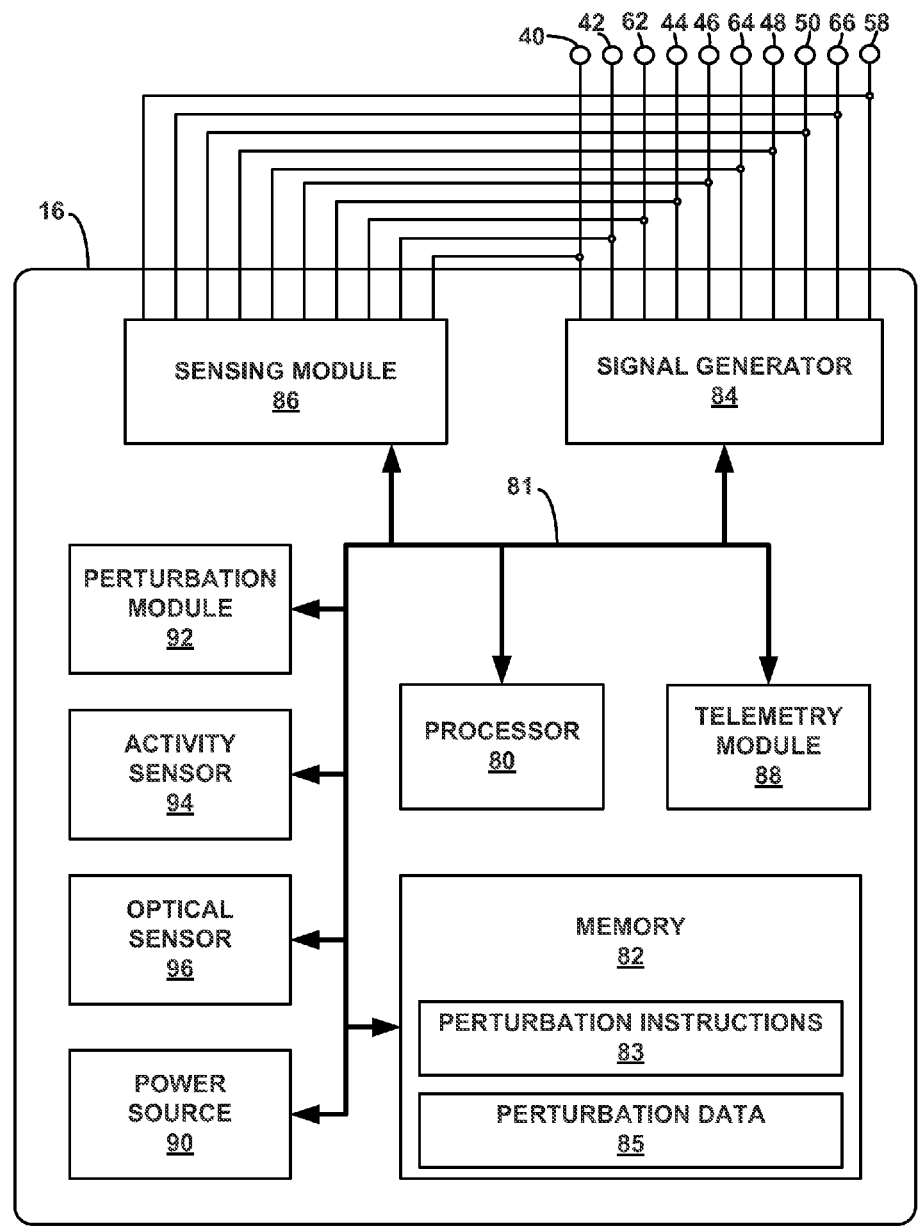
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, perturbation module 92, signal generator 84, sensing module 86, telemetry module 88, activity sensor 94, optical sensor 96, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs. For cardiac pacing therapy, processor 80 may control stimulation generator 84 to deliver electrical pulses according to one or more parameters such as an atrial rate, a ventricular rate, and escape intervals such as an A-V interval, and a V-V interval. Similarly, processor 80 (or perturbation module 92) may also control signal generator 84 to deliver stimulation therapy according to electrical stimulation defined to induce physiological perturbations or deliver baseline electrical stimulation.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus 81, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon as physiological parameters. Sensing may be done to determine heart rates, heart rate variability, arrhythmias, or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus 81.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as VF or VT. These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the anti-tachyarrhythmia pacing. In the event that processor 80 detects an atrial or ventricular tachyarrhythmia based on signals from sensing module 86, and a cardioversion or defibrillation shock is desired, processor 80 may control the amplitude, form and timing of the shock delivered by signal generator 84.

Memory 82 may be configured to store a variety of operational parameters, therapy programs, perturbation instructions, sensed and detected data, and any other information related to the therapy, treatment, and monitoring of patient 14. In the example of FIG. 3, memory 82 also includes perturbation instructions 83 and perturbation data 85. Perturbation instructions 83 may include all of the stimulation parameters and instructions required by processor 80 and perturbation module 92 to induce a physiological perturbation, detect physiological parameters, and generate heart failure status. Perturbation data 85 may store all of the data (e.g., detected or measured physiological parameters obtained in response to the induced physiological perturbation). In this manner, memory 82 may store a plurality of detected physiological parameters as the data required to generate the heart failure status within IMD 16 or after transmission to an external device.

Perturbation instructions 83 may include definitions of each of the physiological parameters detected with perturbation module 92. These definitions may include instructions regarding what electrodes or sensors to use in the detection of each physiological parameter, the sample rate, calibration schemes, and any other related information. In one example, the physiological parameters stored in perturbation instructions 83 may include a thoracic fluid index, an atrial tachycardia or fibrillation burden, a ventricular contraction rate during atrial fibrillation, a patient activity, a nighttime heart rate, a heart rate variability, a cardiac resynchronization therapy percentage, a bradyarrhythmia pacing therapy percentage (in a ventricle and/or atrium) and an electrical shock event. In other examples, other patient physiological parameters may be stored that may be useful in the generation of the heart failure status, e.g., blood pressure, lung volume, lung density, and breathing rate. In such examples, IMD 16 may include or be coupled to sensors known in the art for detecting such parameters. In some examples, the atrial tachycardia or fibrillation burden may be a duration, e.g., an elapsed time, of the event, a percent or amount of time over a certain period, a number of episodes, or even a frequency of episodes.

Perturbation instructions 83 may also include instructions regarding which physiological parameters to detect for the induced physiological perturbation and how to generate the heart failure status. One or more physiological parameters may be selected to be used for the generation of the heart failure status based on the severity of the heart failure, other conditions of patient 14, or other experience of the clinician. The generation of the heart failure status may be performed based on the values of one or more of the physiological parameters. In one example, an absolute value of a detected physiological parameter exceeding one or more thresholds may be used to generate the heart failure status. Each time the detected physiological parameter exceeds another threshold, the heart failure status may increase in severity (e.g., heart failure worsening). In another example, perturbation module 92 may compare a recently detected physiological parameter to past physiological parameters detected from other induced physiological perturbations. When the physiological parameter changes more than a predetermined percentage, perturbation module 92 may change the heart failure status according to the change. In this manner, the heart failure status may be sensitive to relative changes in the physiological parameters over time.

In some examples, processor 80 may transmit the generated heart failure status to programmer 24 and/or a remote computing device after each induced physiological perturbation. In other examples, processor 80 may only transmit the generated heart failure status if the status indicates a significant change in the heart failure status. A significant change in the heart failure may be a heart status moving to a more severe level, or a numerical value at least 10 percent more severe than the previously generated heart failure status. If the heart failure status indicates that patient 14 requires immediate treatment, e.g., admission to a hospital or pharmacological intervention, processor 80 may push the heart failure status to a remote location to facilitate treatment. Alternatively, processor 80 may transmit the physiological parameter data after each induced physiological perturbation for offline analysis and heart failure status generation.

Perturbation data 85 is a portion of memory 82 that may store some or all of the physiological parameter data that is measured and detected by perturbation module 92. Perturbation data 85 may store the data for each physiological parameter on a rolling basis and delete old data as necessary or only for a predetermined period of time, e.g., an evaluation window of perturbations. Processor 80 may access perturbations data 85 when necessary to retrieve and transmit patient physiological parameter data and/or generate a heart failure status. Although perturbation instructions 83 and/or perturbation data 85 may consist of separate physical memories, these components may simply be an allocated portion of the greater memory 82.

Perturbation module 92 may control multiple features of IMD 16. Perturbation module 92 may control signal generator 84 to deliver electrical stimulation selected to induce the physiological perturbation. Perturbation module 92 may determine when to deliver the electrical stimulation and with what values of the stimulation parameters stored in perturbation instructions 83. Perturbation module 92 may also adjust one or more stimulation parameters if the physiological perturbation is not sufficiently induced. In other words, perturbation module 92 may be configured to induce a physiological perturbation in patient 14.

In this manner signal generator 84 may be configured to deliver electrical stimulation to patient 14 according to perturbation module 92 to induce the physiological perturbation. Perturbation module 92 may control signal generator 84 to deliver electrical stimulation configured to induce physiological perturbations in patient 14. This perturbation stimulation may include changes to stimulation therapy such as changes to the atrial pacing rate, ventricular pacing rate, modifications to the atrial-ventricular intervals, modifications to the ventricular-ventricular intervals, suspension of cardiac resynchronization therapy pacing, slowing the heart rate by cardiac electrical window therapy, or any combination thereof. Cardiac electrical window therapy may include stimulating (or exciting) the atria, sino-atrial node, and/or atrioventricular node during the ventricular refractory period to increase the period of time between ventricular contractions. Cardiac electrical window therapy is described in U.S. patent application Ser. No. 12/913,354 filed Oct. 27, 2010 and entitled "SUPRAVENTRICULAR STIMULATION TO CONTROL VENTRICULAR RATE," the entire content of which is incorporated herein by reference. The electrical stimulation may be delivered for a predetermined period of time or as needed to produce detected physiological parameters.

The electrical stimulation delivered by signal generator 84 may be defined by stimulation parameters with at least one value different from the therapy parameters that define stimulation therapy. Generally, the electrical stimulation parameters may have at least one perturbation value that deviates from a therapeutic value of the parameter. The perturbation threshold, e.g., the percentage difference between the therapeutic value and the perturbation value, may be different for different parameters. For example, a pacing rate for perturbation stimulation may differ from a therapeutic pacing rate by a large percentage, but an A-V interval for perturbation stimulation may differ from a therapeutic A-V interval by a relatively small percentage.

Perturbation module 92 may also control the detection of one or more physiological parameters in response to the induced physiological perturbation. For example, perturbation module 92 may measure the thoracic impedance, analyze an electrogram of heart 12, monitor the electrical stimulation therapy delivered to patient 14, or sense the patient activity. Perturbation module 92 may additionally generate a heart failure status based on the detected physiological parameters. The heart failure status may be an absolute indication of the heart failure severity of patient 14 based on the parameters detected in response to the perturbation. The heart failure status may include multiple levels of severity, e.g., healthy, low, medium, and high. Alternatively, the heart failure status may merely be a trend indication, e.g., improving, steady, worsening. The heart failure status may incorporate more or less levels in other examples, but the heart failure status may be an indicator of heart failure using the objectively detected physiological parameters subsequent to the induced physiological perturbation.

It is noted that functions attributed to perturbation module 92 herein may be embodied as software, firmware, hardware or any combination thereof. In some examples, perturbation module 92 may at least partially be a software processor executed by processor 80. In other examples, processor 80 may perform the functions attributed to perturbation module 92 herein. Perturbation module 92 may sense or detect any of the physiological parameters used to generate the heart failure status or otherwise indicate that patient 14 may be susceptible to heart failure. Perturbation module 92 may also compare each of the physiological parameters to respective thresholds defined in perturbation instructions 83. Perturbation module 92 may automatically detect two or more physiological parameters subsequent to, or even prior to, inducing the physiological perturbation.

In one example, perturbation module 92 may analyze electrograms received from sensing module 86 to detect an episode of atrial fibrillation or atrial tachycardia, and determine atrial tachycardia or fibrillation burden, e.g., duration, as well as a ventricular contraction rate during atrial fibrillation to detect the physiological parameter. Perturbation module 92 may also analyze electrograms in conjunction with a real-time clock to determine a nighttime heart rate or a daytime heart rate or a difference between the day and night heart rate, and also analyze electrograms to determine a heart rate variability, or any other detectable cardiac events from one or more electrograms. As described above, perturbation module 92 may use peak detection, interval detection, or other methods to analyze the electrograms.

In addition, perturbation module 92 may include and/or control sensing module 86, activity sensor 94, and optical sensor 96. Sensing module 86 may be used to detect the thoracic impedance used to generate the thoracic fluid index. As described herein, sensing module 86 may utilize any of the electrodes of FIG. 1, 2 or 3 to take intrathoracic impedance measurements. In other examples, sensing module 86 may utilize separate electrodes coupled to IMD 16 or in wireless communication with telemetry module 88. Once sensing module 86 measures the intrathoracic impedance of patient 14, perturbation module 92 may generate the thoracic fluid index and compare the index to a thoracic fluid index threshold defined in perturbation instructions 83 or previously detected thoracic fluid indices from previous physiological perturbations. Any of sensing module 86, activity sensor 94, optical sensor 96, or other sensors may be considered a sensing module configured to detect at least one physiological parameter of the patient subsequent to inducement of the physiological perturbation.

Activity sensor 94 may include one or more accelerometers or other devices capable of detecting motion and/or position of patient 14. Activity sensor 94 may therefore detect activities of patient 14 or postures engaged by patient 14. For example, activity sensor 94 may provide signals that allow perturbation module 92 to differentiate between a rest state and an active state of patient 14. In this manner, perturbation module 92 may monitor the patient activity based on the magnitude and/or duration of accelerations detected by activity sensor 94. Perturbation module 92 may then compare magnitudes and/or durations of accelerations from different activities to determine the relative exertion of each particular activity engaged by patient 14. The patient activity may thus be used to generate the heart failure status.

In addition, the patient activity may be used to determine when to deliver the electrical stimulation that induces the physiological perturbation. In one example, perturbation module 92 may be configured to detect an active state of patient 14 based on data detected by activity sensor 94, e.g., an activity module. Perturbation module 92 may then be configured to induce the physiological perturbation in patient 14 during this active state. Alternatively, perturbation module 92 may induce the physiological perturbation when activity sensor 94 indicates patient 14 is in a rest state.

Perturbation module 92 may also control and receive measurements from additional sensors. For example, perturbation module 92 may collect optical measurements from optical sensor 96 indicative of blood oxygenation. Perturbation module 92 may control alternative or additional sensors contained within IMD 16. For example, IMD 16 may include one or more respiration sensors, chemical sensors, pressure sensors, temperature sensors, or any other sensors that may detect a physiological parameter of patient 14.

In addition to detecting parameters of patient 14, perturbation module 92 may also control certain stimulations, e.g., perturbations, therapies, or baseline stimulations, delivered by processor 80 and signal generator 84. Furthermore, perturbation module 92 may monitor signals through signal generator 84 or receive therapy information directly from processor 80 for the detection of delivered therapy as a physiological parameter of a patient that is responsive to perturbation stimulation. Example physiological parameters detected by this method may include a cardiac resynchronization therapy percentage and an electrical shock event.

The cardiac resynchronization therapy (CRT) percentage may be the amount of time each day, for example, IMD 16 delivers CRT pacing to heart 12. Low therapy percentages may indicate that beneficial therapy is not being delivered and that adjustment of therapy parameters, e.g., a decreased atrioventricular delay or an increased pacing rate, may improve therapy efficacy. In one example, higher therapy percentages may indicate that heart 12 is sufficiently pumping blood through the vasculature with the aid of therapy to prevent fluid buildup. In other examples, higher therapy percentages may indicate that heart 12 is unable to keep up with blood flow requirements. An electrical shock may be a defibrillation event or other high energy shock used to return heart 12 to a normal rhythm. Perturbation module 92 may detect these physiological parameters as well and compare them to a cardiac resynchronization therapy percentage and shock event threshold, respectively, defined in perturbation instructions 83 to determine how each parameter may contribute to the heart failure status.

Perturbation module 92 may include additional sub-modules or sub-routines that detect and monitor other physiological parameters used to monitor patient 14 and/or generate the heart failure status. In some examples, perturbation module 92, or portions thereof, may be incorporated into processor 80 or sensing module 86. In other examples, raw data used to produce physiological parameter values may be stored in perturbation data 85 for later processing or transmission to an external device. An external device may then produce each physiological parameter from the raw data, e.g., electrogram or intrathoracic impedance. In other examples, perturbation module 92 may additionally receive data from one or more implanted or external devices used to detect each metric such that IMD 16 stores the perturbation data.

Perturbation module 92 may generate the heart failure status based upon the detected physiological parameters and stored in perturbation data 85 of memory 82. For example, perturbation module 92 may continually update the heart failure status as perturbation module 92 updates each physiological parameter subsequent to the induced perturbation. In other examples, perturbation module 92 may periodically update the heart failure status after a perturbation is completed. Perturbation module 92 may compare each of the automatically detected physiological parameters to their respective thresholds or previously detected parameter values and automatically generate the heart failure status based on the comparison.

In other examples, the heart failure status may be generated with a processor of an external computing device, e.g. programmer 24 or external server. However, perturbation module 92 may still collect and store the data for each physiological parameter or even organize and format the detected physiological parameters before transmitting the parameters in perturbation data 85 to the external device. In addition, processor 80 may transmit the parameters detected from previous perturbations, the time of day of the detected parameters, the activity state of patient 14, or any other relevant information for generating the heart failure status of patient 14.

Processor 80 may provide an alert to a user, e.g., of programmer 24, regarding the data from any physiological parameter and/or the heart failure status. In one example, processor 80 may provide an alert with the heart failure status when programmer 24 or another device communicates with IMD 16. In other examples, processor 80 may push an alert to programmer 24 or another device whenever the heart failure status indicates heart failure worsening to a predetermined degree via transmission by telemetry module 88. Alternatively, IMD 16 may directly indicate to patient 14 that medical treatment is needed due to a worsening heart failure status. IMD 16 may include a speaker to emit an audible sound through the skin of patient 14 or a vibration module that vibrates to notify patient 14 of needed medical attention. Processor 80 may choose this action, for example, if the alert cannot be sent because of a lack of an available connection.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus 81. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert, heart failure status, and/or detected physiological parameters through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., detected physiological parameters or heart failure status, to the user.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

In alternative embodiments, IMD 16 may automatically provide therapy to patient 14 based on the heart failure status and/or one of the detected physiological parameters. For example, IMD 16 or another device may include a drug pump that delivers a dose of medication, e.g., nitroglycerin, to alleviate the imminent or present heart failure conditions. This drug pump may be in addition to or in place of electrical stimulation therapy devices. In other examples, IMD 16 may deliver pacing therapy, or adjusted pacing therapy, to try and reduce the heart failure symptoms. Processor 80 may control the automatic delivery of therapy by IMD 16 based on the heart failure status.

Figure 4:
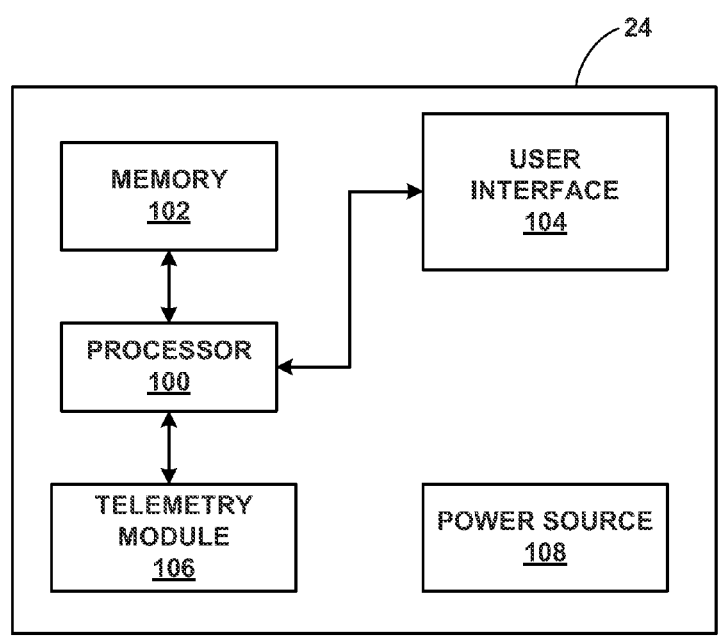
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). Programmer 24 may also be used to review detected physiological parameters, the heart failure status of patient 14, or even adjust one or more stimulation parameters that defines the perturbation stimulation. The clinician may interact with programmer 24 via user interface 104, which may include display to present graphical user interface to a user, and a keypad or another mechanism for receiving input from a user. In addition, the user may receive an alert or notification from IMD 16 indicating the heart failure risk score and/or patient metrics via programmer 24.

Processor 100 can take the form of one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may receive an alert or notification of the heart failure status from telemetry module 88 of IMD 16. The alert may be automatically transmitted, or pushed, by IMD 16 when the heart failure status worsens to a predetermined degree. In addition, the alert may be a notification to a healthcare professional, e.g., a clinician or nurse, of the risk score and/or an instruction to patient 14 to seek medical treatment for the potential heart failure condition. In response to receiving the alert, user interface 104 may present the alert to the healthcare professional regarding the heart failure status or present an instruction to patient 14 to seek medical treatment.

Either in response to pushed heart failure information, e.g., the status or physiological parameters, or requested heart failure information, user interface 104 may present the detected physiological parameters and/or the heart failure status to the user. In some examples, user interface 104 may also highlight the one or more physiological parameter values that have exceeded a respective threshold or otherwise varied from previously detected parameter values. In this manner, the user may quickly review those physiological parameters that have contributed to a worsening heart failure status. This same information may be presented to the user when the heart failure status is stable or improves in some examples.

Upon receiving the alert via user interface 104, the user may also interact with user interface 104 to cancel the alert, forward the alert, retrieve data regarding the heart failure status (e.g., patient physiological parameter data), modify the physiological perturbation instructions, or conduct any other action related to the treatment of patient 14. In some examples, the clinician may be able to review raw data to diagnose any other problems with patient 14. User interface 104 may even suggest treatment along with the alert, e.g., certain drugs and doses, to minimize symptoms and tissue damage that could result from heart failure. User interface 104 may also allow the user to specify the type and timing of alerts based upon the severity of the heart failure status. In addition to the heart failure status, user interface 104 may also provide the underlying parameters to allow the clinician to monitor therapy efficacy and remaining patient conditions.

In some examples, processor 100 of programmer 24 and/or one or more processors of one or more networked computers may perform all or a portion of the techniques described herein with respect to processor 80, perturbation module 92, and IMD 16. For example, processor 100 or a metric detection module within programmer 24 may analyze detected physiological parameters, the associated thresholds or previously detected parameter values, and/or generate a heart failure status.

Figure 5:
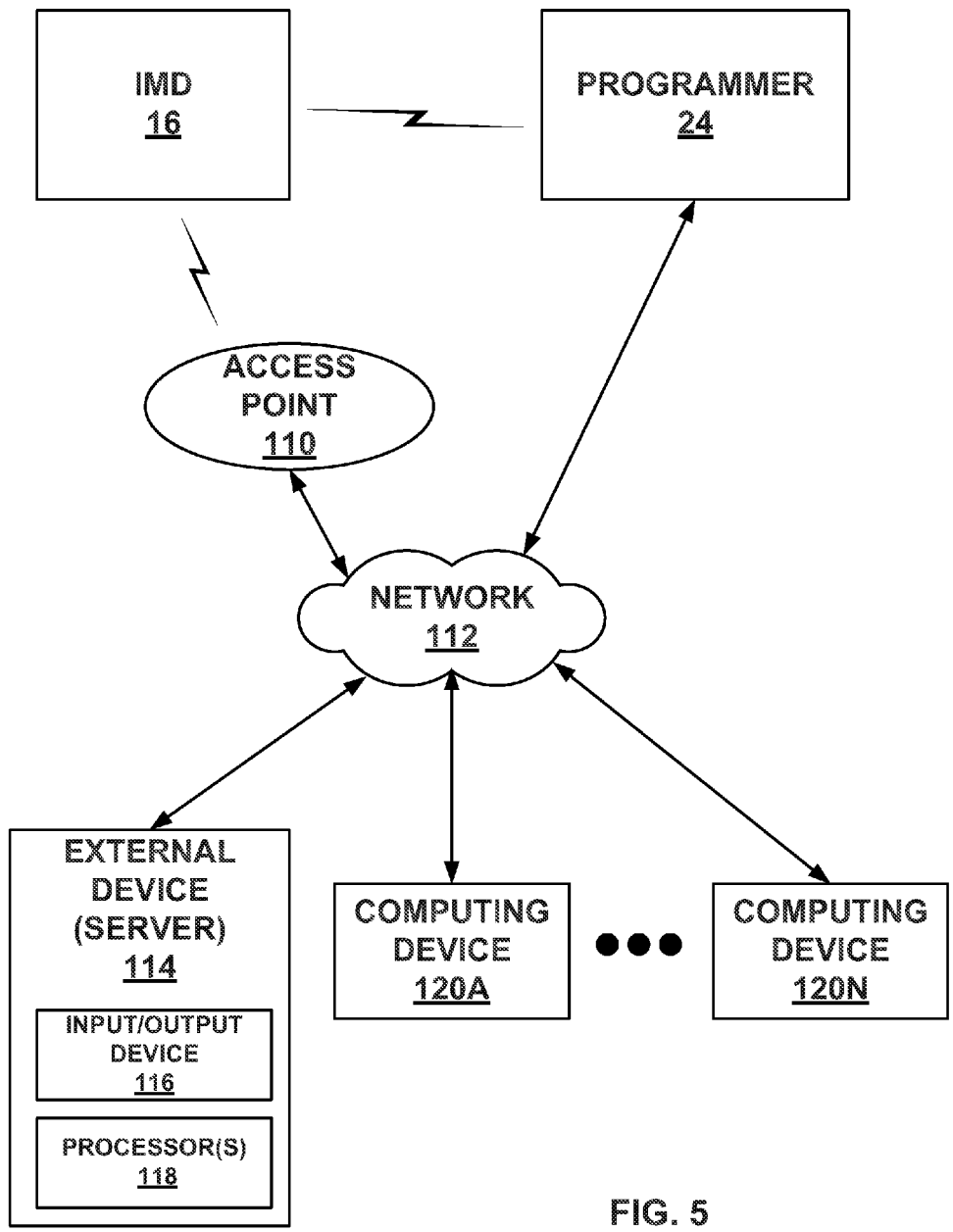
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 114, and one or more computing devices 120A-120N, that are coupled to the IMD 16 and programmer 24 shown in FIG. 1 via a network 112. Network 112 may be used to transmit the detected physiological parameter data, the heart failure status, or any other information from IMD 16 to another external computing device. In this example, IMD 16 may use its telemetry module 88 to communicate with programmer 24 via a first wireless connection, and to communication with an access point 110 via a second wireless connection. In the example of FIG. 5, access point 110, programmer 24, server 114, and computing devices 120A-120N are interconnected, and able to communicate with each other, through network 112. In some cases, one or more of access point 110, programmer 24, server 114, and computing devices 120A-120N may be coupled to network 112 through one or more wireless connections. IMD 16, programmer 24, server 114, and computing devices 120A-120N may each comprise one or more processors, such as one or more microprocessors, DSPs, ASICs, FPGAs, programmable logic circuitry, or the like, that may perform various functions and operations, such as those described herein. Server 114 may include input/output device 116 and processors(s) 118.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, server 114 or computing devices 120 may control or perform any of the various functions or operations described herein with respect to IMD 16 or programmer 24, e.g., generate a heart failure status based on the detected physiological parameters, determine perturbation stimulation parameter, or make adjustments to therapy parameters.

In some cases, server 114 may be configured to provide a secure storage site for archival of detected physiological parameter data and heart failure status that has been collected and generated from IMD 16 and/or programmer 24. Network 112 may comprise a local area network, wide area network, or global network, such as the Internet. In some cases, programmer 24 or server 114 may assemble sensing integrity information in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

In the manner of FIG. 5, computing device 120A or programmer 24, for example, may be remote computing devices that receive and present the heart failure status from IMDs so that a clinician can remotely monitor the condition of patient 16. In addition, remote monitoring may allow a single clinician or clinic to monitor multiple patients so that a clinician may prioritize those patients needing treatment immediately. In other words, the clinician may triage patients by analyzing the heart failure status of multiple patients. The computing device may use its communication module to receive the heart failure status from multiple IMDs via network 112. In this manner, each heart failure status is representative of one of the patients. Although the IMDs may transmit the heart failure status at any time, generally the IMDs may transmit a heart failure status when the status indicates that heart failure is worsening. This method may useful for healthcare professionals making house calls, serving patients within a nursing home, or any other circumstance in which a professional treats many patients.

As described above, IMD 16 may transmit a generated heart failure status to a clinician when the heart failure status indicates that heart failure is worsening and patient 16 may require modified therapy. The heart failure status may be transmitted when the status exceeds an absolute threshold, such as another lever higher in severity (e.g., going from a moderate to severe heart failure status). Alternatively, a numerical heart failure status may be transmitted when the heart failure status worsens by a predetermined percentage of the previous heart failure status. In this manner, only substantial changes in the heart failure status may trigger transmission of the heart failure status to the clinician via network 112. When a heart failure status is transmitted, IMD 16 may also transmit the values of the detected physiological parameter, and in some examples, prior detected values as well.

In addition to transmitting data and heart failure status to remote users, network 112 may allow external devices to provide computing power to analyze detected physiological parameters and generate the heart failure status. For certain computationally intensive tasks, IMD 16 may consume valuable power and/or not be capable of timely analysis. In some examples, IMD 16 may be capable of performing simple calculations, but more thorough analysis may be performed by an external computing device. Therefore, IMD 16 may transmit some or all of detected physiological parameter data to external device 114, for example. External device 114 may then perform the analysis, or command another computing device to perform at least a portion of the analysis, and distribute the resulting analysis and/or heart failure status to the clinician. In addition, external device 114 may transmit the analyzed data back to IMD 16 to allow IMD 16 to store a record of the data and/or use the analyzed data to adjust the stimulation parameters of the perturbation stimulation, adjust therapy parameters of the stimulation therapy, or identify trends in detected parameters of the heart failure status for patient 14.

IMD 16 may also utilize network 112 to notify the clinician of completed or proposed changes to therapy parameters that define stimulation therapy. In some examples, IMD 16 may send proposed changes to one or more therapy parameters to the clinician. IMD 16 may only incorporate the changes once IMD 16 receives approval from the clinician. Alternatively, IMD 16 may notify the clinician that one or more therapy parameters have been adjusted based on the detected response of the physiological parameters subsequent to the induced physiological perturbation. If the clinician does not approve of the new therapy parameters, the clinician may override the therapy parameter adjustment and transmit updated therapy parameters. IMD 16 may then receive the updated therapy parameters from a remote computing device (e.g., computing device 120A) via network 112 and incorporate the updated therapy parameters for use in delivering stimulation therapy. In this manner, IMD 16 may be at least partially remotely controlled by the clinician over network 112.

Figure 6:
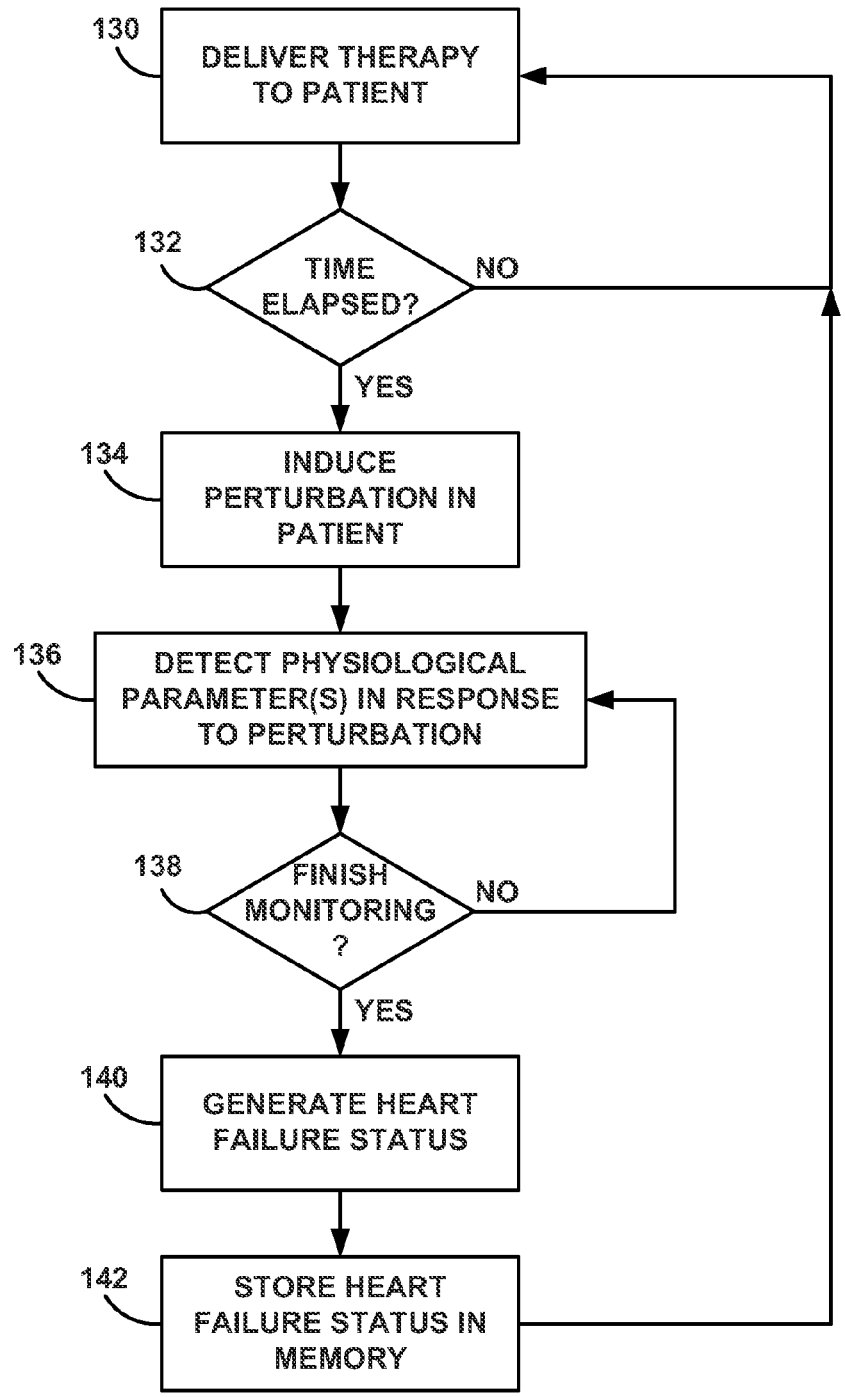
FIG. 6 is a flow diagram of an example method for generating a heart failure status based on detection of patient parameters in response to a physiological perturbation.

FIG. 6 is a flow diagram of an example method for generating a heart failure status based on detection of patient parameters in response to a physiological perturbation. FIG. 6 will be described with components of IMD 16 both detecting physiological parameters and generating the heart failure status for the patient, but in other examples, the example method may be performed, at least in part, by other devices (e.g., programmer 24 and/or an external computing device).

During normal operation of IMD 16, signal generator 84 may deliver stimulation therapy to patient 16, e.g., cardiac pacing or cardiac resynchronization therapy (130). However, in other examples, therapy may include different stimulation or therapy, or IMD 16 may monitor patient 14 without providing therapy. If perturbation module 92 determines that the time for inducing the physiological perturbation has not elapsed or occurred ("NO" branch of block 132), signal generator 84 may continue to deliver stimulation therapy to patient 14. If perturbation module 92 determines that the time has elapsed or occurred to induce the physiological perturbation ("YES" branch of block 132), then perturbation module 92 may control signal generator 84 to deliver electrical stimulation selected to induce the physiological perturbation in patient 14 (134).

The time elapsed may be tracked by perturbation module 92 as the amount of time that has lapsed since the previous induced physiological perturbation. This time may generally be between approximately one hour and one week. More specifically, the elapsed time may be between approximately 12 hours and 48 hours. In one example, the elapsed time may be approximately 24 hours from the previous physiological perturbation. Instead of an elapsed time, the induced physiological perturbation may be scheduled to occur at a predetermined date and time. For example, perturbation module 92 may be scheduled to induce the physiological perturbation every hour, twice a day, once a day, once a week, or at randomly scheduled times.

In addition, perturbation module 92 may be configured to induce the physiological perturbation at particular times of day. For example, it may be beneficial to induce physiological perturbations at approximately the same time of day to minimize the potential variable effect of time of day on the response of the physiological parameters to the perturbation. In one example, perturbation module 92 may be configured to induce the physiological perturbation at night when patient 14 is asleep. When asleep, other physiological factors may not influence the patient's response to the perturbation. Since patient 14 may not be able to sense the induced perturbation, this event may not interfere with regular sleep patterns. Alternatively, perturbation module 92 may induce the physiological perturbation in response to a detected physiological parameter, with or without a lock-out period beginning from the previously induced physiological perturbation.

As described herein, perturbation module 92 may induce the physiological perturbation in patient 14 by delivering electrical stimulation that deviates from the stimulation therapy otherwise delivered to patient 14. For example, the electrical stimulation to induce physiological perturbations may deviate from stimulation therapy with changes to the atrial pacing rate, ventricular pacing rate, modifications to the atrial-ventricular intervals, modifications to the ventricular-ventricular intervals, e.g., in the case of CRT, suspension of cardiac resynchronization therapy pacing, slowing the heart rate by cardiac electrical window therapy, or any combination thereof. The electrical stimulation delivered to patient 14 may be delivered for a predetermined amount of time such that the physiological perturbation is induced. This predetermined period of time may be between approximately one second and several hours. More specifically, the electrical stimulation may be delivered between approximately 30 seconds and 5 minutes. However, IMD 16 may deliver electrical stimulation of any duration necessary to induce a physiological perturbation. Although a single physiological perturbation is described herein, this perturbation may include multiple perturbations or a perturbation that varies over time in response to the electrical stimulation.

Once the physiological perturbation is induced, or the electrical stimulation has been initiated, perturbation module 92 may detect one or more physiological parameters using one or more sensors (136). In some examples, perturbation module 92 may begin detecting the one or more physiological parameters prior to inducing the physiological perturbation such that perturbation module 92 may monitor any changes to detected parameters caused by the perturbation. If perturbation module 92 is not finished monitoring for detected parameters ("NO" branch of block 138), perturbation module 92 may continue to detect the physiological parameters (136). Once perturbation module 92 is finished monitoring for the physiological parameters ("YES" branch of block 138), perturbation module 92 may generate the heart failure status (140). Perturbation module 92 may compare the values of the detected physiological parameters to one or more thresholds and/or compare the values of recently detected parameters to values of physiological parameters detected in response to previous physiological perturbations.

Perturbation module 92 may then store the generated heart failure status in memory 82 (142). Perturbation module 92 may also control telemetry module 88 to transmit the heart failure status to a programmer 24 and/or a remote device. Processor 80 may then control signal generator 84 to continue to deliver therapy to patient 14.

Figure 7:
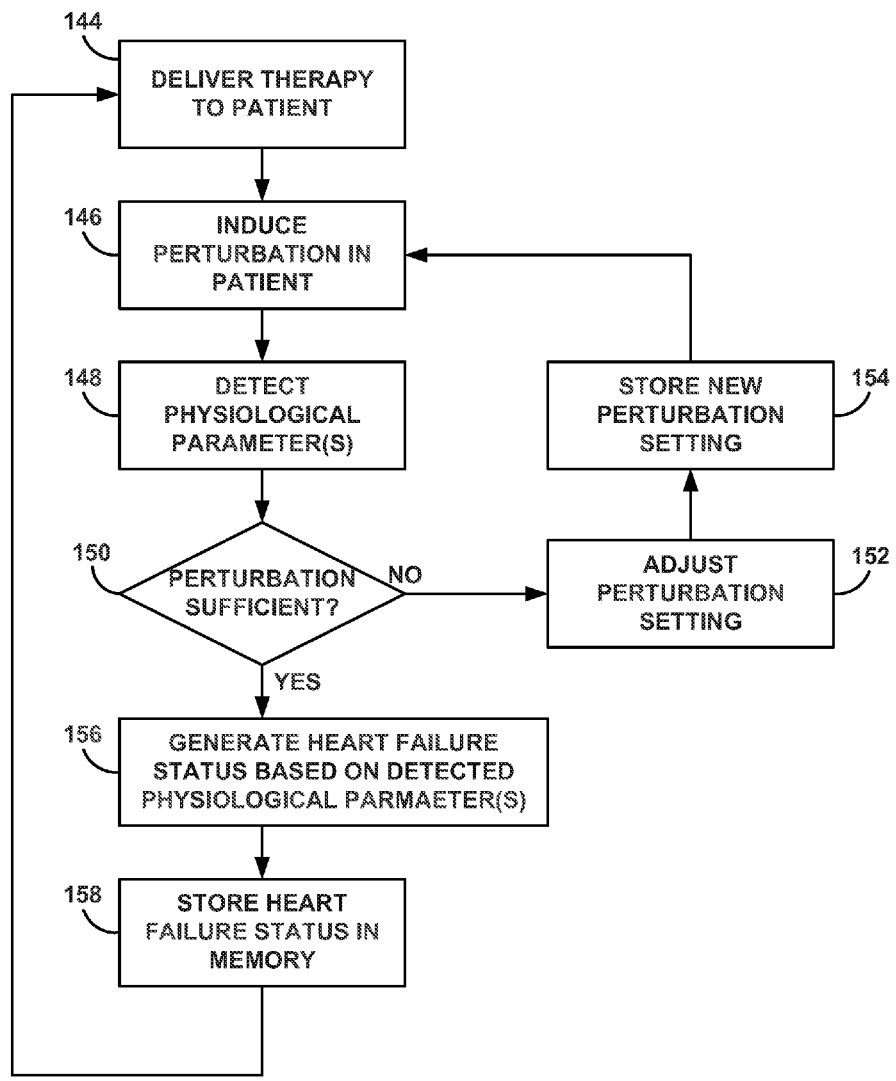
FIG. 7 is a flow diagram of an example method for adjusting perturbation settings for inducing a physiological perturbation in a patient.

FIG. 7 is a flow diagram of an example method for adjusting perturbation settings for inducing a physiological perturbation in a patient. FIG. 7 will be described with components of IMD 16 detecting physiological parameters, generating the heart failure status for the patient, and adjusting perturbation settings, but in other examples, the example method may be performed, at least in part, by other devices (e.g., programmer 24 and/or an external computing device).

Signal generator 84 may deliver therapy to patient 14 as defined by stored therapy instructions (144). Perturbation module 92 may then control signal generator 84 to deliver electrical stimulation to induce a physiological perturbation in patient 14 once perturbation module 92 is instructed to deliver the stimulation (146). Perturbation module 92 may subsequently detect one or more physiological parameters to monitor the perturbation (148). If the perturbation was sufficient for identifying the heart failure status of patient 14 ("YES" branch of block 150), then perturbation module 92 generates the heart failure status based on the detected physiological parameters (156).

If the perturbation was not sufficient to identify the heart failure status of patient 14 ("NO" branch of block 150), perturbation module 92 may adjust a perturbation setting that defines the electrical stimulation (152). Perturbation module 92 may be configured to adjust a value of at least one stimulation parameter that defines the electrical stimulation for perturbations based on the detected at least one physiological parameter. Insufficient perturbations may include circumstances in which there were no detected changes in the physiological parameters. Perturbation module 92 may then increase the deviation of one or more stimulation parameters that defines the perturbation stimulation. For example, perturbation module 92 may decrease a pacing rate and/or increase an interval. Parameters that may be adjusted may include an atrial rate, a ventricular rate, escape intervals such as an A-V interval, a V-V interval (in the case of CRT), or other parameters that define the perturbation stimulation. Alternatively, insufficient perturbations may be those perturbations where detected physiological parameters change so much that feedback mechanisms other than the heart failure condition may be influencing the physiological parameters. In this case, perturbation module 92 may reduce the deviation of the perturbation stimulation from stimulation therapy. Perturbation module 92 may then store the one or more adjusted value for electrical stimulation delivery, or stimulation parameter, in memory 82 (154). Perturbation module 92 may request immediate re-delivery of electrical stimulation with the adjusted parameters (146). Alternatively, perturbation module 92 may control delivery of the electrical stimulation with the adjusted parameters at the next scheduled perturbation inducement.

Once perturbation module 92 generates the heart failure status based on one or more detected physiological parameters (156), perturbation module 92 may store the heart failure status in memory 82 (158). Depending upon the severity of the heart failure status, perturbation module 92 may also control telemetry module 88 to transmit the heart failure status to programmer 24 and/or a remote device. Processor 80 may then continue to control the delivery of stimulation therapy to patient 14 (144).

Figure 8:
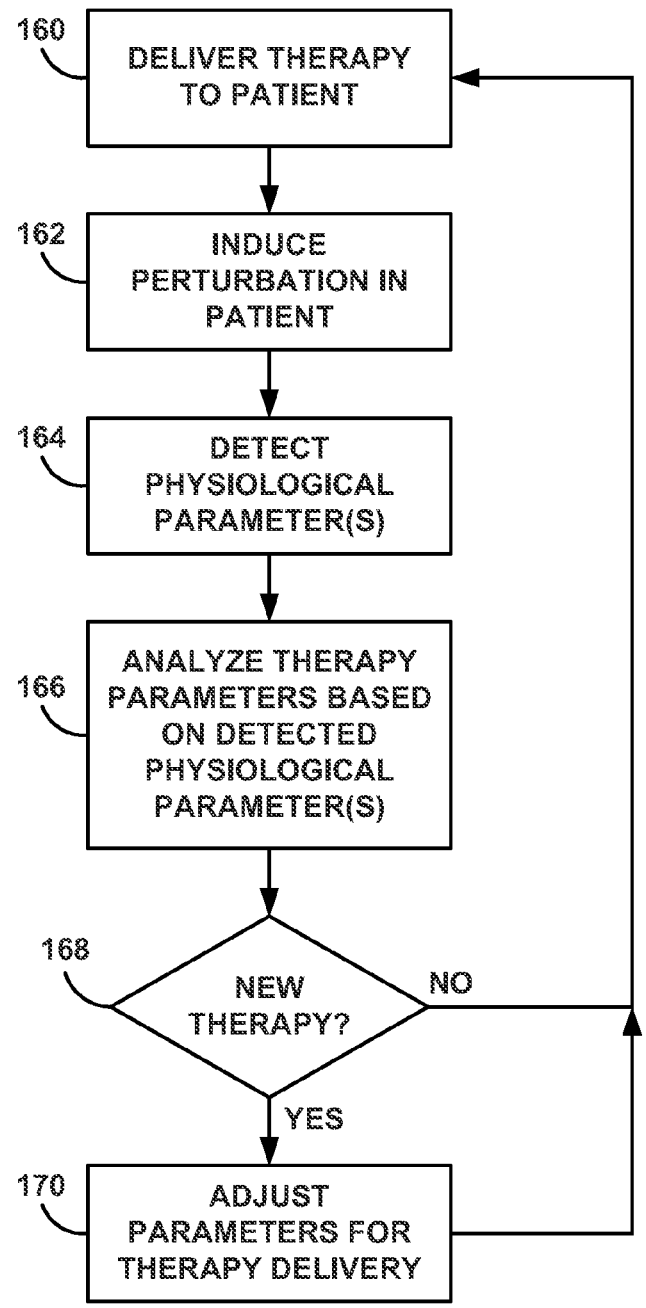
FIG. 8 is a flow diagram of an example method for adjusting therapy parameters based on patient parameters detected after inducing a physiological perturbation in a patient.

FIG. 8 is a flow diagram of an example method for adjusting therapy parameters based on patient parameters detected after inducing a physiological perturbation in a patient. FIG. 8 will be described with components of IMD 16 detecting physiological parameters, generating the heart failure status for the patient, and adjusting therapy parameters, but in other examples, the example method may be performed, at least in part, by other devices (e.g., programmer 24 and/or an external computing device).

Processor 80 may control signal generator 84 to deliver therapy to patient 14 as defined by stored therapy instructions (160). Perturbation module 92 may then control signal generator 84 deliver electrical stimulation to induce a physiological perturbation in patient 14 once perturbation module 92 is instructed to deliver the stimulation (162). Perturbation module 92 may subsequently, or continually, detect one or more physiological parameters to monitor the perturbation (164).

Perturbation module 92 may then analyze the therapy parameters of the stimulation therapy based on the physiological parameters detected in response to the physiological perturbation (166). Perturbation module 92 may determine if the detected therapy parameters indicate that the stimulation therapy is still effective at treating patient 16 and/or the therapy could be improved. For example, perturbation module 92 may determine that a decrease in heart rate variability may indicate that therapy parameters could be adjusted to increase pacing sensitivity to patient activity. In addition, perturbation module 92 may adjust a stimulation therapy parameter based on the generated heart failure status. In this manner, perturbation module 92 may be configured to adjust at least one of a plurality of therapy parameters that define stimulation therapy based on at least one of the detected physiological parameter and the heart failure status.

If perturbation module 92 determines that no new therapy parameters are needed ("NO" branch of block 168), perturbation module 92 may indicate to processor 80 that therapy may continue as defined (160). If perturbation module 92 determines that one or more therapy parameters need to be adjusted ("YES" branch of block 168), perturbation module 92 may adjust the one or more identified stimulation parameters for subsequent therapy delivery (170). Perturbation instructions 85 may store instructions, formulas, look up tables, equations, or other information that perturbation module 92 uses as a guide in determining if a therapy parameter should be adjusted based on the detected physiological parameters.

Figure 9:
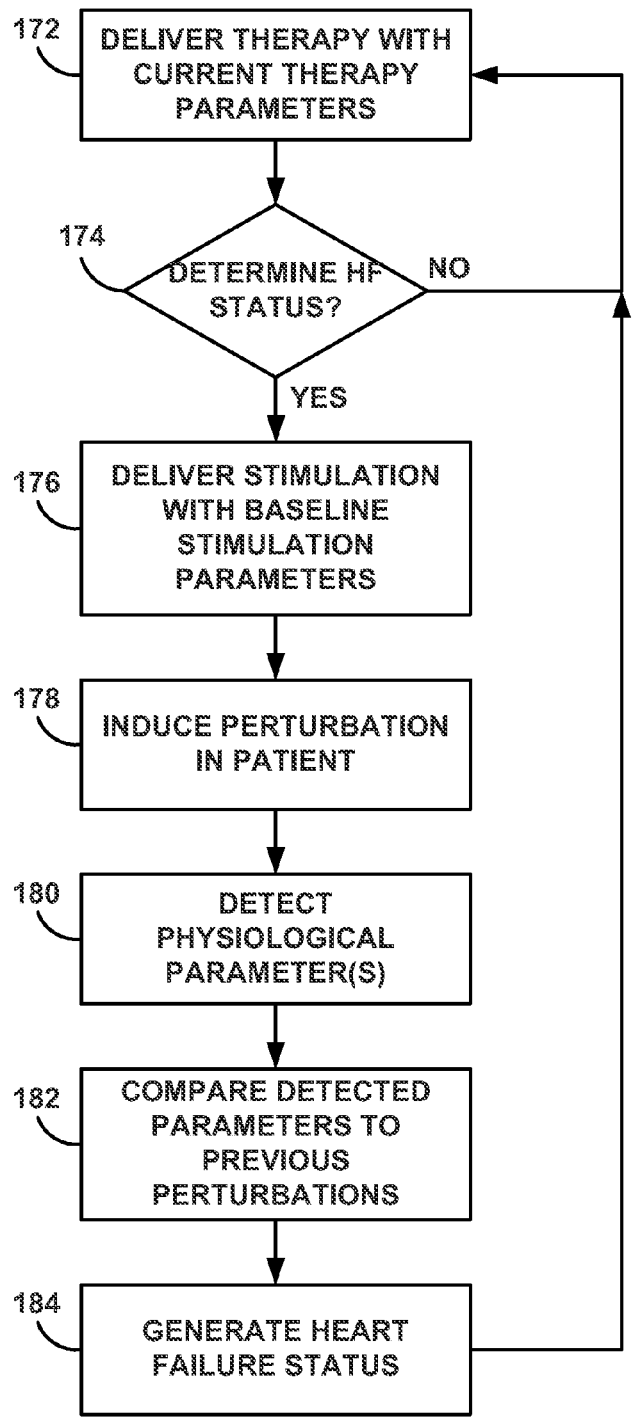
FIG. 9 is a flow diagram of an example method for delivering a baseline stimulation therapy prior to inducing a physiological perturbation in a patient.

FIG. 9 is a flow diagram of an example method for delivering a baseline stimulation therapy prior to inducing a physiological perturbation in patient 14. FIG. 9 will be described with components of IMD 16 detecting physiological parameters, generating the heart failure status for the patient, and adjusting therapy parameters, but in other examples, the example method may be performed, at least in part, by other devices (e.g., programmer 24 and/or an external computing device).

Processor 80 may control signal generator 84 to deliver therapy to patient 14 as defined by currently stored therapy parameters (172). If perturbation module 92 is to determine heart failure status (e.g., induce a physiological perturbation in patient 14) ("NO" branch of block 174), signal generator 84 may continue to deliver therapy to patient 14 (172). If perturbation module 92 is to determine heart failure status ("YES" branch of block 174), perturbation module 92 controls signal generator 84 to deliver baseline electrical stimulation to patient 14 defined by baseline therapy parameters (176). Signal generator 84 may be configured to deliver baseline electrical stimulation to the patient prior to delivering electrical stimulation that induces the physiological perturbation.

The baseline electrical stimulation may be stimulation that remains constant over the entire period therapy and is delivered to patient 14 with IMD 16 (e.g., the stimulation parameters of the baseline electrical stimulation are typically not changed). Since therapy parameters may change over time as the condition of patient 14 changes, this therapy may vary the responsiveness of patient 14 to an induced physiological perturbation. In other words, a perturbation induced after delivering one form of stimulation therapy may be different than a perturbation induced after delivering a second form of stimulation therapy. To reduce this effect on the induced perturbation as therapy changes over time, perturbation module 92 may control signal generator 84 to deliver a consistent, or baseline, electrical stimulation prior to each time that electrical stimulation directed to induce the physiological perturbation is delivered. Although the baseline stimulation may be a therapy, e.g., the initial therapy delivered to patient 14, the baseline stimulation may not be directed to providing any therapy to patient 14. Perturbation module 92 may be configured to define the baseline electrical stimulation with preselected therapy parameters that establish this repeatable baseline electrical stimulation prior to each inducement of the physiological perturbation.

The baseline electrical stimulation may be delivered for a predetermined period of time or until one or more detected physiological parameter values become stable. Then, perturbation module 92 may control signal generator 84 to deliver the electrical stimulation to induce the physiological perturbation (178). Perturbation module 92 may subsequently, or continually, detect one or more physiological parameters to monitor the perturbation (180). Perturbation module 92 may then compare the detected physiological parameters to physiological parameters associated with previously induced perturbations (182). Using the comparison, perturbation module 92 generates the heart failure status for the record and/or transmission to programmer 24 or a remote device (184). Processor 80 may then continue to control signal generator 84 to deliver therapy (172).

In other examples, the detected physiological parameters may be compared to one or more thresholds for generating the heart failure status. In some examples, physiological parameters detected during the baseline stimulation may be compared to physiological parameters detected after inducing the physiological perturbation. Perturbation module 92 may initiate physiological parameter detection prior to, or just after, initiating the baseline electrical stimulation. Then, perturbation module 92 may obtain physiological parameters for when patient 14 is in the known steady state of the baseline stimulation and in response to the physiological perturbation. The change in one or more of these detected physiological parameter values between the baseline stimulation and the induced perturbation may be used to generate the heart failure status.

The techniques described herein allow an IMD to monitor the heart failure progress of a patient by inducing a repeatable physiological perturbation. Therefore, IMD may automatically generate a heart failure status of a patient while reducing the effects of any subjective or uncontrollable elements. The heart failure status may be automatically generated using the data obtained from detected physiological parameters after inducing the physiological perturbation. The heart failure status and/or other parameter data may be reviewed by a clinician, even remotely. In this manner, the clinician may be able to continually monitor the patient's condition without physically evaluating the patient. This remote heart failure monitoring system may decrease treatment response time, improve the quality of life of the patient, and possibly extend the life of the patient.

Various examples have been described that include delivering electrical stimulation, detecting and storing patient parameters and generating a heart failure status. These examples include techniques for identifying patients with changing heart failure conditions. In addition, an alert of the status may be remotely delivered to a healthcare professional for earlier diagnosis and/or treatment of heart failure. Any combination of detection and notification of heart failure is contemplated. These and other examples are within the scope of the following claims.

The invention claimed is:

1. A method comprising:
   delivering an electrical stimulation therapy to a patient's heart defined by current therapy parameter values for treating a condition of the patient;
   inducing a physiological perturbation by:
      delivering a baseline electrical stimulation to the patient's heart defined by an initial therapy delivered to the patient and comprising at least one baseline therapy parameter different than the current therapy parameters;
      after delivering the baseline electrical stimulation, inducing the physiological perturbation in the patient by delivering electrical stimulation to the patient's heart comprising a stimulation parameter having a perturbation value that deviates from a therapeutic value;
   detecting a physiological parameter in response to the induced physiological perturbation;
   comparing the physiological parameter to a physiological parameter detected during a previously induced perturbation;
   generating, by one or more processors, a heart failure status based on the detected change in the at least one physiological parameter; and
   adjusting the current therapy parameters used to deliver the electrical stimulation therapy in response to the generated heart failure status.

2. The method of claim 1, wherein inducing the physiological perturbation comprises delivering the electrical stimulation comprising a stimulation parameter having the perturbation value to the patient for a predetermined period of time.

3. The method of claim 1, wherein the stimulation parameter having the perturbation value comprises at least one of an atrial rate, a ventricular rate, an A-V interval, a V-V interval.

4. The method of claim 1, further comprising adjusting, based on the detected change in the at least one physiological parameter, a value of at least one stimulation parameter that defines the electrical stimulation configured to induce the physiological perturbation.

5. The method of claim 1, further comprising adjusting at least one of a plurality of therapy parameters that define the electrical stimulation therapy based on at least one of the detected change to the physiological parameter or the heart failure status.

6. The method of claim 1, further comprising detecting an active state of the patient, wherein inducing the physiological perturbation comprises inducing the physiological perturbation during the active state.

7. The method of claim 1, further comprising detecting a rest state of the patient, wherein inducing the physiological perturbation comprises inducing the physiological perturbation during the rest state.

8. A system comprising:
   a signal generator;
   a processor configured to control the signal generator to deliver an electrical stimulation therapy to a patient's heart defined by current therapy parameter values for treating a condition of the patient;
   a perturbation module configured to induce a physiological perturbation in the patient by:
      delivering a baseline electrical stimulation to the patient's heart defined by an initial therapy delivered to the patient and comprising at least one baseline therapy parameter different than the current therapy parameters;
      after delivering the baseline electrical stimulation, inducing the physiological perturbation in the patient by delivering electrical stimulation to the patient's heart comprising a stimulation parameter having a perturbation value that deviates from a therapeutic value; and
   a sensing module configured to detect a change in at least one physiological parameter of the patient in response to the induced physiological perturbation, wherein the perturbation module is configured to generate a heart failure status based on the change to the at least one physiological parameter.

9. The system of claim 8, further comprising a signal generator configured to deliver the electrical stimulation comprising the stimulation parameter having the perturbation value for a predetermined period of time.

10. The system of claim 8, wherein the stimulation parameter having the perturbation value comprises at least one of an atrial rate, a ventricular rate, an A-V interval, and a V-V interval.

11. The system of claim 8, wherein the perturbation module is configured to adjust, based on the detected change to the at least one physiological parameter, a value of at least one stimulation parameter that defines the electrical stimulation configured to induce the physiological perturbation.

12. The system of claim 8, wherein the perturbation module is configured to adjust at least one of a plurality of therapy parameters that define the stimulation therapy based on at least one of the detected change to the physiological parameter or the heart failure status.

13. The system of claim 8, further comprising an activity module configured to detect an active state of the patient, wherein the perturbation module is configured to induce the physiological perturbation in the patient during the active state.

14. The system of claim 8, further comprising an activity module configured to detect a rest state of the patient, wherein the perturbation module is configured to induce the physiological perturbation in the patient during the rest state.

15. A system comprising:
   means for delivering an electrical stimulation therapy to a patient's heart defined by current therapy parameter values for treating a condition of the patient;
   means for inducing a physiological perturbation in a patient by:
      delivering a baseline electrical stimulation to the patient's heart defined by an initial therapy delivered to the patient and comprising at least one baseline therapy parameter different than the current therapy parameters;
      after delivering the baseline electrical stimulation, inducing the physiological perturbation in the patient by delivering electrical stimulation to the patient's heart comprising a stimulation parameter having a perturbation value that deviates from a therapeutic value;
   means for detecting a change in at least one physiological parameter of the patient in response to the induced physiological perturbation; and
   means for generating a heart failure status based on the change to the at least one physiological parameter.

16. The system of claim 15, the means for inducing the physiological perturbation comprises means for delivering the electrical stimulation comprising the stimulation parameter having the perturbation value to the patient for a predetermined period of time.

* * * * *